United States Patent [19]

Stasz et al.

[11] Patent Number: 4,850,353
[45] Date of Patent: Jul. 25, 1989

[54] SILICON NITRIDE ELECTROSURGICAL BLADE

[75] Inventors: Peter Stasz, Moundsview; Jeffrey J. Solberg, Northfield; Scott R. Grabinger, Maple Grove, all of Minn.

[73] Assignee: Everest Medical Corporation, Brooklyn Center, Minn.

[21] Appl. No.: 229,432

[22] Filed: Aug. 8, 1988

[51] Int. Cl.$^4$ .............................................. A61B 17/36
[52] U.S. Cl. ........................... 128/303.14; 128/303.17
[58] Field of Search ...................... 128/303.13–303.17; 604/22

[56] References Cited

U.S. PATENT DOCUMENTS

| | | | |
|---|---|---|---|
| 4,074,718 | 2/1978 | Morrison | 128/303.14 |
| 4,161,950 | 7/1979 | Doss et al. | 128/303.14 |
| 4,202,337 | 5/1980 | Hren et al. | 128/303.14 |
| 4,232,676 | 11/1980 | Herczog | 128/303.14 |
| 4,248,231 | 2/1981 | Herczog et al. | 128/303.14 |
| 4,314,559 | 2/1982 | Allen | 128/303.14 |
| 4,802,476 | 2/1989 | Noerenberg et al. | 128/303.17 |

*Primary Examiner*—Max Hindenburg
*Attorney, Agent, or Firm*—Orrin M. Haugen; Thomas J. Nikolai; Frederick W. Niebuhr

[57] ABSTRACT

An electrosurgical blade having a silicon nitride ceramic substrate having a beveled working edge with first and second conductive metal traces adhered to opposed side surfaces of the substrate along the working edge so as to be closely spaced relative to one another across the thickness dimension of the beveled working edge. Further conductive traces are formed on opposed sides of the substrate along the other edge of the substrate. In use, when a high RF voltage is applied between the traces extending along the working edge and the surgical blade is brought into contact with tissue, the relatively high current density causes relatively high heating to take place, bursting the cells and creating an incision. When a high RF voltage is applied between the traces separated by the width dimension of the substrate, the current density therebetween is significantly lower but sufficient to create enough heat to dehydrate tissue and blood cells whereby coagulation is achieved. The use of silicon nitride as the substrate material enhances the performance of the blade by inhibiting thermal runaway.

10 Claims, 1 Drawing Sheet

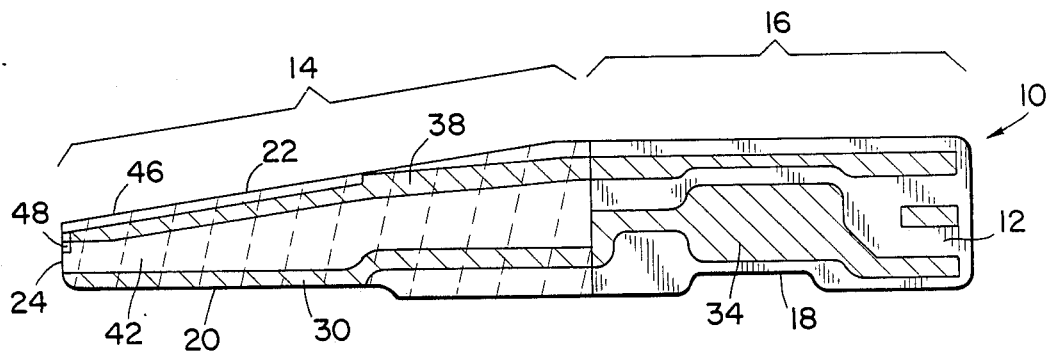
Fig. 1
Fig. 4
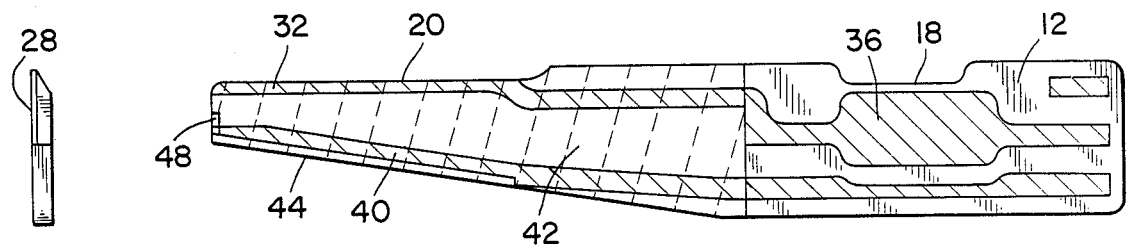
Fig. 3
Fig. 2

SILICON NITRIDE ELECTROSURGICAL BLADE

BACKGROUND OF THE INVENTION

I. Field of the Invention: This invention relates generally to an electrosurgical instrument, and more particularly to an improved blade construction for effecting cutting and coagulation during an electrosurgical procedure.

II. Discussion of the Prior Art: In carrying out electrosurgical procedures, a special scalpel is used which is adapted to be energized by a radio frequency voltage source for cutting tissue and/or coagulating blood through cauterization. Such scalpels commonly incorporate a conductive blade and the RF energy source is connected between that blade and a large area patient plate which is made to abut the skin of the patient at a site generally remote from the location of the surgery. In that arrangement, the system is said to be a "monopolar system". Problems have arisen in using such monopolar systems due to the frequency with which patients suffer burns at the site of the patient plate.

In an attempt to obviate such problems, electrosurgical scalpels have been designed utilizing bipolar blades where first and second conductive electrodes are placed along a sharpened cutting edge on opposite sides of the blade and when a high frequency, high voltage RF energy source is connected across the strip electrodes and brought into contact with tissue, an electrical arc is established which rapidly dehydrates the tissue cells causing them to burst and creating an incision as the blade is drawn across the tissue.

In the Doss et al U.S. Pat. No. 4,161,950, there is described an electrosurgical knife in which the blade is formed using a ceramic substrate which is sharpened to a knife edge and deposited on opposed sides of that substrate and extending close to but short of the apex of the cutting edge are conductive electrodes, preferably formed from tungsten applied using a screening process. The Hren et. al. Pat. No. 4,202,337 also recommends the use of a ceramic substrate for an electrosurgical blade with aluminum oxide ($Al_2O_3$) being recommended.

We have found, however, that many ceramic materials including $Al_2O_3$ do not possess optimum characteristics for use in the fabrication of electrosurgical blades. When it is considered that the arc produced temperatures may often exceed 1000° C. at the local level, it is important that the volume resistivity versus temperature characteristics be high enough at the arc temperature so that the blade substrate material is not destroyed in our avalanche mode of operation. That is to say, if the substrate material used for the electrosurgical blade exhibits a significant drop in volume resistivity with increasing temperature, a point may be reached where the resistance of the substrate drops to such a low value that the $I^2R$ loss at radio frequencies increases the blade's temperature even further to the point where an avalanche condition exists, destroying the substrate material and/or the electrode traces formed thereon. Because of this avalanche effect, prior art electrosurgical blades have relied on a sharpened edge to perform mechanical cutting and the RF heating is employed strictly for coagulation. Power levels are limited to a range which does not produce arcing since the resulting high temperatures are destructive of the substrate material.

Furthermore, alumina oxide ceramics tend to be quite brittle and are subject to undue breakage when formed into thin, blade-like substrates. Even modest pressures encountered during electrosurgical procedures have been found sufficient to snap such prior art blades.

SUMMARY OF THE INVENTION

In accordance with the present invention, an improved electrosurgical blade is constructed of a ceramic material which exhibits an extremely high volume resistivity over a broad temperature range as compared to prior art blades. Specifically, we have found that by using a special silicon nitride formulation referred to as Ceralloy 147-3 available through Ceradyne, Inc. of Costa Mesa, Calif., retains its high volume resistivity over a temperature range greater than the aluminum oxide ($Al_2O_3$). The silicon nitride is also more resistant to breakage than the aluminum oxide material.

In addition to the material itself, the blade of the present invention is also physically configured to enhance its use as a R.F. electrical cutting instrument and as an instrument for coagulation. The blade includes a working portion and a handle engaging portion with the working portion including a beveled working edge and an unbeveled opposed edge, the two being separated at the distal end by a blunt but beveled tip. Conductive traces formed from a suitable refractory metal are adhered to and extend parallel to the working edge on opposed side surfaces of the silicon nitride ceramic substrate and, thus, are separated from one another by the thickness of the substrate at the beveled working edge. An additional conductive trace is adhered to and extends parallel to the unbeveled opposed edge of the silicon nitride substrate so as to be spaced a relatively large distance from the traces extending along the beveled working edge. All of the traces extend over the handle receiving portion of the blade where they are adapted to mate with electrical contacts contained within the handle. These contacts, in turn, are adapted to be coupled to a source of radio frequency energy. When the energization is between the traces running along the working edge of the substrate and tissue is allowed to bridge between the two traces, the resulting current flow through the tissue results in rapid internal heating and bursting of cells, thus creating an incision as the blade is drawn across the tissue. When the RF energy is applied between the relatively spaced traces at the blunt tip of the blade, the current density is reduced to the point where heating and coagulation take place, but not so as to cause further cutting.

It has also been found expedient to at least partially coat the working portion of the blade with an insulating layer such as silicon dioxide such that only a very narrow conductive electrode is exposed at, but not across, the working edge.

OBJECTS

It is accordingly a principal object of the present invention to provide an improved blade for an electrosurgical scalpel.

Another object of the invention is to provide a bipolar blade for an electrosurgical scalpel comprising a ceramic substrate exhibiting relatively high volume resistivity over a wide temperature range and a high resistance to breakage.

Yet another object of the invention is to provide a blade for an electrosurgical scalpel having a silicon nitride substrate with metal conductive traces exhibiting a high melting point extending along the working edge on opposed sides of the substrate so as to remain isolated from one another only by the thickness of the substrate at the working edge.

A still further object of the invention is to provide an improved blade for an electrosurgical scalpel in which provision is made for allowing the blade to be used in either a cutting or a coagulating mode.

DESCRIPTION OF THE DRAWINGS

The foregoing objects and advantages of the invention will become apparent to those skilled in the art from the following detailed description of a preferred embodiment, especially when considered in conjunction with the accompanying drawings in which like numerals in the several views refer to corresponding parts.

FIG. 1 is a front view of an electrosurgical scalpel blade in accordance with the present invention;

FIG. 2 is a rear view of the blade of FIG. 1;

FIG. 3 is a distal end view of the blade of FIG. 1; and

FIG. 4 is a bottom view of the blade of FIG. 1.

DESCRIPTION OF THE PREFERRED EMBODIMENT

With reference to FIG. 1, the electrosurgical blade of the present invention is indicated generally by numeral 10 and is seen to comprise a ceramic substrate 12 which is preferably a material exhibiting a relatively high volume resistivity over a substantial temperature range, with silicon nitride ceramic being preferred. The ceramic blank or substrate 12 has an integrally joined distal working portion identified by the bracket 14 and a handle receiving portion identified by bracket 16. That is to say, the electrosurgical blade 10 is intended to be inserted into a handle (not shown) which may, for example, be of the type described in a co-pending application of Marc D. Noerenberg, et al, Ser. No. 56,434, filed June 1, 1987, and entitled "ELECTRO-SURGICAL BLADE". As is explained in that application, the handle is effective to firmly grip the blade 10 and to apply the requisite electrical voltages to the conductive patterns or traces formed on the blade, the configuration of which are yet to be described. In addition, the handle incorporates a piezoelectric crystal which is arranged to abut the handle receiving portion 16 of the blade to impart high frequency vibrations thereto whereby cavitation results, aiding in preventing the buildup of burned tissue and other debris on the blade.

As illustrated in FIGS. 1 and 2, the handle receiving portion 16 is generally rectangular, except for a registration notch 18 formed inwardly from the lower edge thereof. The working portion 14 of the blade includes a working edge 20 and an opposed edge 22 which converges toward the working edge 20 but terminating at a blunt distal tip 24.

As can best be seen in the views of FIGS. 3 and 4, the working edge 20 of the blade is ground to provide a beveled edge as indicated by numeral 26. Furthermore, the blunt tip 24 is also beveled as indicated by numeral 28.

The silicon nitride substrate heretofore described is also provided with a pattern of metallization in the form of conductive traces which may be realized using known hybrid circuit techniques. In particular, refractory metals such as tungsten, titanium, nickel, molybdenum, manganese and alloys thereof may be applied in accordance with a predetermined pattern utilizing silk screening techniques or vacuum sputtering through a suitable mask.

With principal reference to FIGS. 1 and 2, it can be noted that first and second conductive traces 30 and 32 are made to extend parallel to the working edge 20 on opposed side surfaces of the silicon nitride ceramic substrate so as to be spaced from one another solely by the thickness of the substrate at the beveled working edge, at least over the working portion 14 of the blade. The strips or traces 30 and 32 also extend substantially across the handle receiving portion 16 of the blade with the pattern including a conductive pad area 34 and 36 of a substantially greater width than the remainder.

Extending along the opposed edge 22 on either side of the substrate are conductive traces 38 and 40 which are formed from the same materials and using the same processes used in adhering the traces 30 and 32 to the silicon nitride substrate 12. Both the traces 38 and 40 extend generally the full length of the blade's working portion 14 and handle receiving portion 16. This allows electrical connections to be made through the handle to an electrosurgical generator. The connector in the handle also electrically joins traces 38 and 40 in common.

The working portion 14 of the blade may, as an option, be provided with a coating of a suitable insulating material such as silicon dioxide. This coating is identified by numeral 42 and, when employed, is present on both sides of the blade so as to substantially cover the ceramic substrate 12 and the metallized tracings 30–32 and 38–40. Subsequently, the working edge 20 will typically be back-ground to expose the underlying metallization along the beveled edge 20 thereof. In a like fashion, a portion of the coating 42 along the opposed edge 22 of the blade is ground away, as at 44 and 46, to expose the underlying metallized traces 38 and 40. The coating layer 42 is also removed over a small area 48 of the tip 24 to expose the underlying conductive trace 40 and 38 at that location.

When in use, the blade shown in FIG. 1 is inserted into a suitable handle (not shown) whereby RF voltages may selectively be applied between the traces 30 and 32 extending along the beveled edge of the working portion 14 of the blade. Because of the very close spacing between the conductive strips which are separated only by the thickness dimension of the substrate at the beveled working edge 20, a relatively high current density exists along that working edge so that when the scalpel blade is brought into contact with tissue to be cut, a relatively large current will flow through the tissue causing the cells coming in contact with the blade to burst and, as the blade is drawn along the tissue, an incision is thereby created.

By operating a suitable switch disposed on the scalpel handle, an RF voltage can be created between the traces 30 and 32, to produce cutting and between traces 32 and 30–40 to produce coagulation. Because of the relatively large spacings between these traces, the current density at the tip 24 is considerably lower than that existing across the traces 30 and 32 during a cutting operation. When the tip portion 24 is touched against a severed blood vessel, sufficient heat is created to dehydrate the tissue, resulting in coagulation and clotting of the severed vessel.

Because silicon nitride is used as the substrate material, the substrate exhibits a relatively high volume resistivity over a significant temperature range. For example, tests of blades made in accordance with the present invention and using a silicon nitride material available through the Ceradyne Corporation, the material exhibited a resistance in excess of 200 megohms up to a temperature of 500° C. while maintaining a resistance of 3.6 megohms at a temperature of 800° C. Because of the high volume resistivity exhibited by the ceramic material, problems of thermal runaway are greatly minimized. That is to say, the material does not break down significantly so as to cause such high parasitic currents to flow through the ceramic which would further deteriorate the resistance characteristics of the material, at least at nominal operating voltages, power levels and arcing conditions.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A blade for an electrosurgical scalpel comprising:
   (a) a relatively thin, silicon nitride ceramic substrate having a working portion and a handle engaging portion, said working portion having a beveled working edge, an unbeveled opposed edge and a blunt beveled tip extending between said working edge and said opposed edge;
   (b) first and second refractory metal conductive strips adhered to and extending parallel to said working edge on opposed side surfaces of said silicon nitride ceramic substrate so as to be spaced from one another by the thickness of said substrate at said beveled working edge in said working portion and extending substantially across said handle receiving portion; and
   (c) a third refractory metal conductive strip adhered to and extending parallel to said unbeveled opposed edge on at least one side surface of said silicon nitride ceramic substrate so as to be spaced a relatively large distance from the first conductive strip, said third conductive strip extending substantially across said handle receiving portion.

2. The blade as in claim 1 and further including a coating of an inorganic, high temperature, electrically nonconductive dielectric material covering said working portion.

3. The blade as in claim 2 wherein said material is silicon dioxide.

4. The blade as in claim 2 wherein said material is silicon nitride.

5. The blade as in claim 2 wherein said material is a high temperature glass.

6. The blade as in claim 2 wherein said coating is eliminated from a predetermined area of the distal end of said working portion, exposing a portion of said third conductive strip.

7. The blade as in claim 1 and further including a fourth refractory metal conductive strip extending over said working portion and parallel to said third conductive strip on the side of said silicon nitride ceramic substrate opposite to said one side surface.

8. The blade as in claim 1 and further including a generally rectangular notch formed in said handle engaging portion of said silicon nitride ceramic substrate.

9. The blade as in claim 7 wherein said fourth refractory metal conductive strip extends substantially across the length dimension of said handle engaging portion.

10. The blade as in claim 7 wherein said first, second, third and fourth conductive strips are formed from metals are selected from the group including silver, gold, molybdenum, manganese, titanium, tungsten, nickel and alloys thereof.

* * * * *